United States Patent [19]
McIntyre et al.

[11] Patent Number: 5,833,707
[45] Date of Patent: Nov. 10, 1998

[54] REMOVABLE STENT AND METHOD OF DEPLOYMENT

[75] Inventors: John McIntyre, Redwood City; Geoffrey A. Orth, La Granada; Peter S. Brown, Mountain View, all of Calif.

[73] Assignee: Advanced Cardiovascular Systems, Inc., Santa Clara, Calif.

[21] Appl. No.: 498,506

[22] Filed: Jul. 5, 1995

[51] Int. Cl.$^6$ .................................................. A61M 29/00
[52] U.S. Cl. ............................... 606/198; 606/108; 623/1
[58] Field of Search ................................. 606/151–156, 606/191, 198, 108; 623/1; 604/96–103

[56] References Cited

U.S. PATENT DOCUMENTS

| | | |
|---|---|---|
| 4,740,207 | 4/1988 | Kreamer . |
| 4,762,128 | 8/1988 | Rosenbluth . |
| 4,877,030 | 10/1989 | Beck et al. . |
| 4,969,890 | 11/1990 | Sugita et al. . |
| 5,037,427 | 8/1991 | Harada et al. . |
| 5,059,211 | 10/1991 | Stack et al. . |
| 5,065,751 | 11/1991 | Wolf . |
| 5,078,726 | 1/1992 | Kreamer . |
| 5,089,006 | 2/1992 | Stiles . |
| 5,100,429 | 3/1992 | Sinofsky et al. . |
| 5,147,385 | 9/1992 | Beck et al. . |
| 5,192,297 | 3/1993 | Hull . |
| 5,192,307 | 3/1993 | Wall . |
| 5,242,451 | 9/1993 | Harada et al. . |
| 5,306,286 | 4/1994 | Stack et al. . |
| 5,306,294 | 4/1994 | Winston et al. . |
| 5,312,339 | 5/1994 | Boussignac et al. . |
| 5,354,309 | 10/1994 | Schnepp-Pesch et al. . |
| 5,383,926 | 1/1995 | Lock et al. . |

OTHER PUBLICATIONS

Yachia, D.; The Use of Urethral Stents for the Treatment of Urethral Strictures, *Annales d'Urologie*, No. 4, pp. 245–252, Jun. 1993.

Morgentaler A. and DeWolf, W. C.; A Self–Expanding Prostatic Stent for Bladder Outlet Obstruction in High Risk Patients, *The Journal of Urology*, vol. 150, 1636–1640, Nov. 1993.

Kirby, R. and Christmas, T., *Benign Prostatic Hyperplasia*, Chapter 7: Interventional Treatment Options, pp. 57–72, 1993.

InSTENT, Inc.™: New Flexibility in Management of Urethral Strictures, 1993.

Microvasive® Boston Scientifc Corporation, Ultraflex™ *Urethral Stent System*, 1994.

Surface Engineering Technologies, a Division of InnerDyne, Inc., Brochure, 1994.

Videotape: New Treatment for Urethral Strictures: A Permanently Implanted Stent, Ortho–McNeil AVA Video.

Nordling, Benign Prostatic Hyperplasia, *Balloons and Stents*, pp. 547–560. 1994.

Gottfried, H.W., et al.: Initial Experiences With the Memotherm Stent in Treatment of Benign Prostatic Hyperplasia (Abstract), *Annales d'Urologie*, 34(2), Mar. 1995.

Spire Corporation; Spi–Argent ™II, (Undated) Brochure.

*Primary Examiner*—Michael Buiz
*Assistant Examiner*—Nancy Mulcare
*Attorney, Agent, or Firm*—Fulwider Patton Lee & Utecht, LLP

[57] ABSTRACT

An apparatus and method for temporarily implanting an intraluminal stent in a body lumen and its subsequent removal. A stent is formed from a thin sheet that has been wound around itself into a generally cylindrical roll. The stent has a deployed configuration with a deployed diameter generally the size of the lumen diameter. The stent has a delivery configuration, formed by winding the stent more tightly than the deployed configuration, with the delivery diameter smaller than the deployed diameter in order to allow low profile delivery into the body lumen. The stent will transform from the delivery configuration to the deployed configuration when exposed to body heat. The stent can be deployed by an intraluminal delivery catheter that secures the stent in its delivery configuration during intraluminal delivery of the stent. The stent can be removed from the body lumen via a removal catheter that coils the stent into a sheath at the end of the removal catheter.

12 Claims, 7 Drawing Sheets

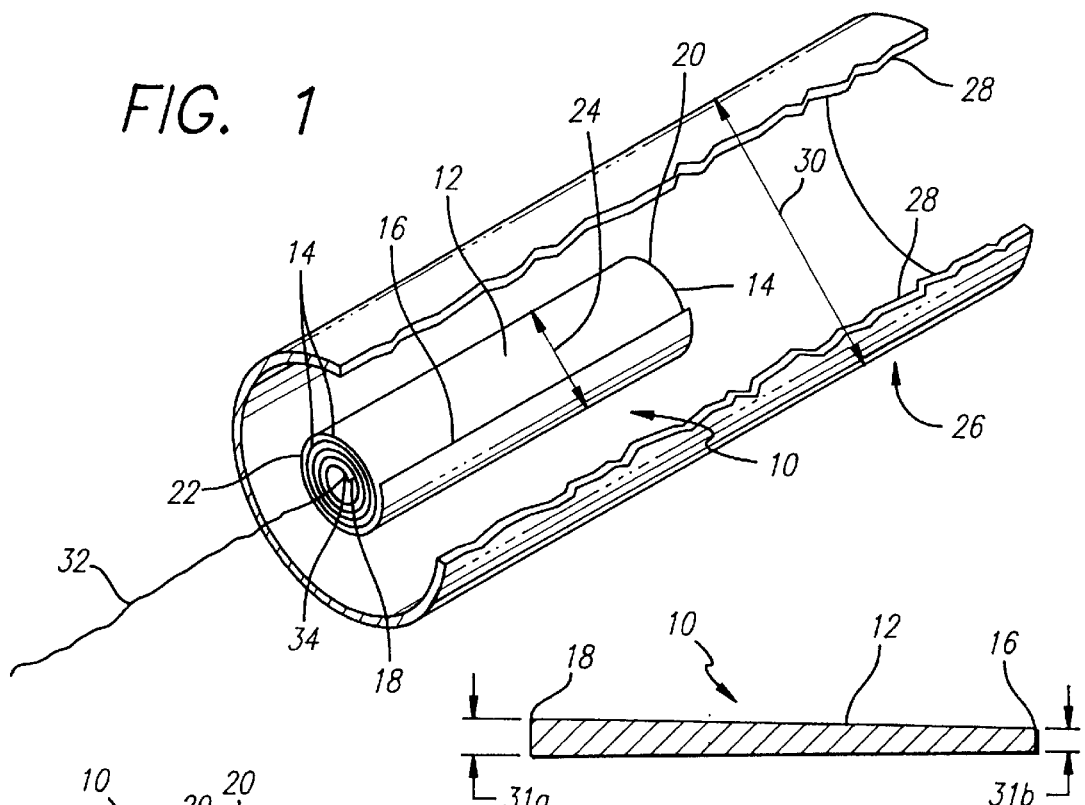
FIG. 1
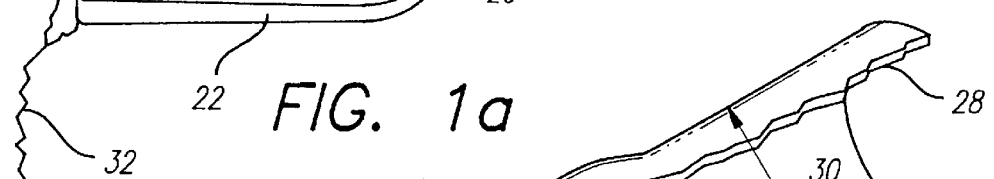
FIG. 1b
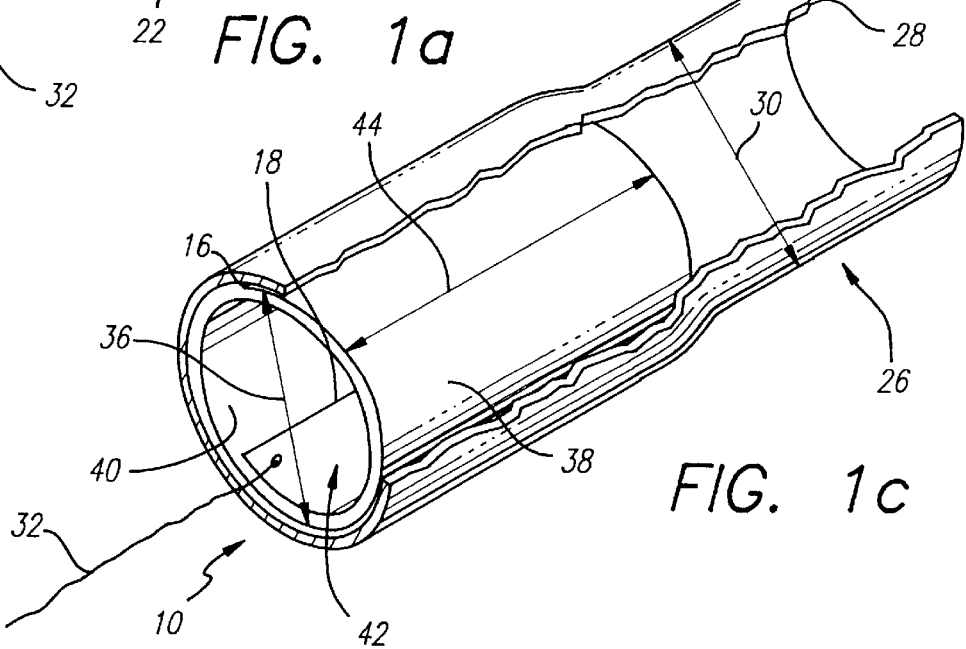
FIG. 1a
FIG. 1c

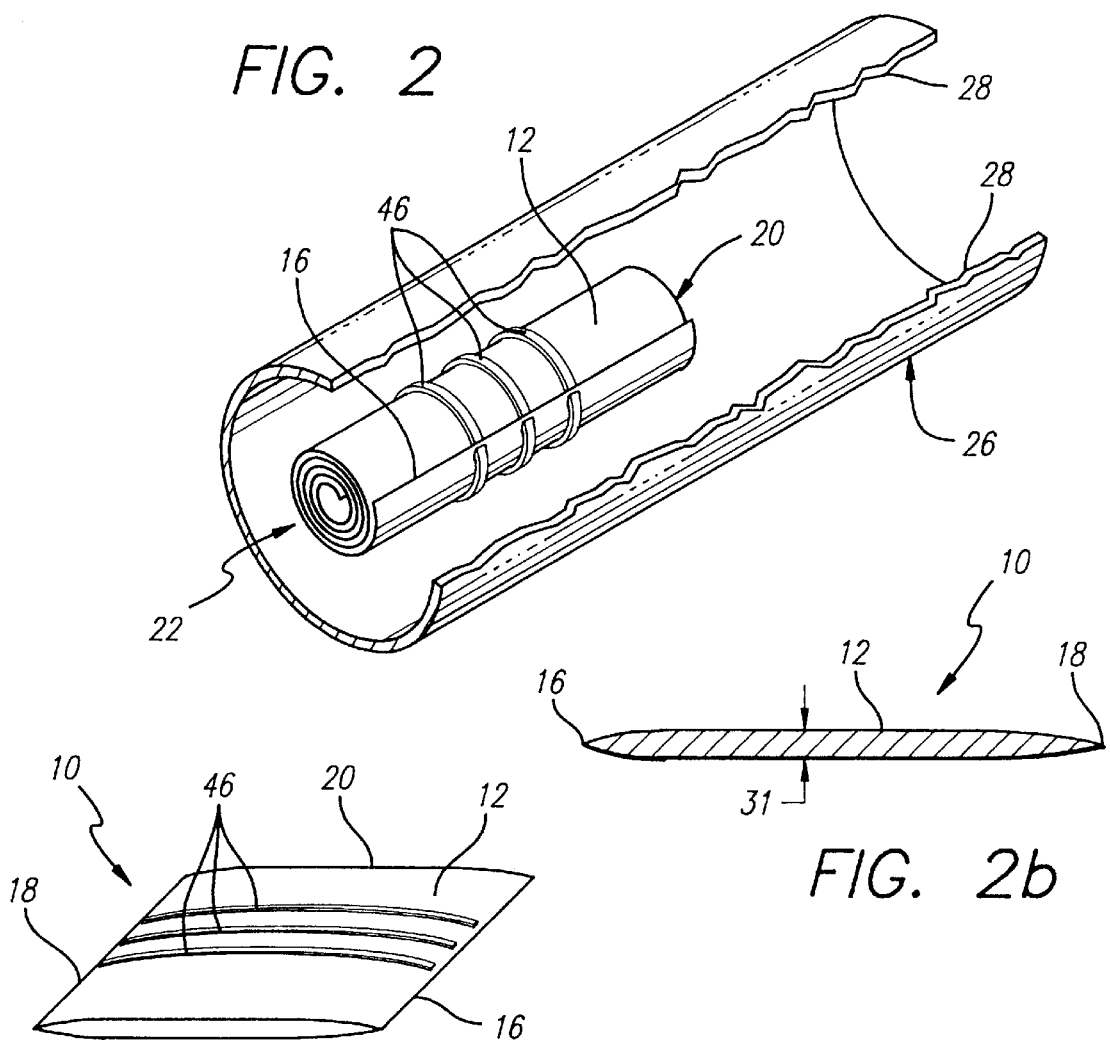
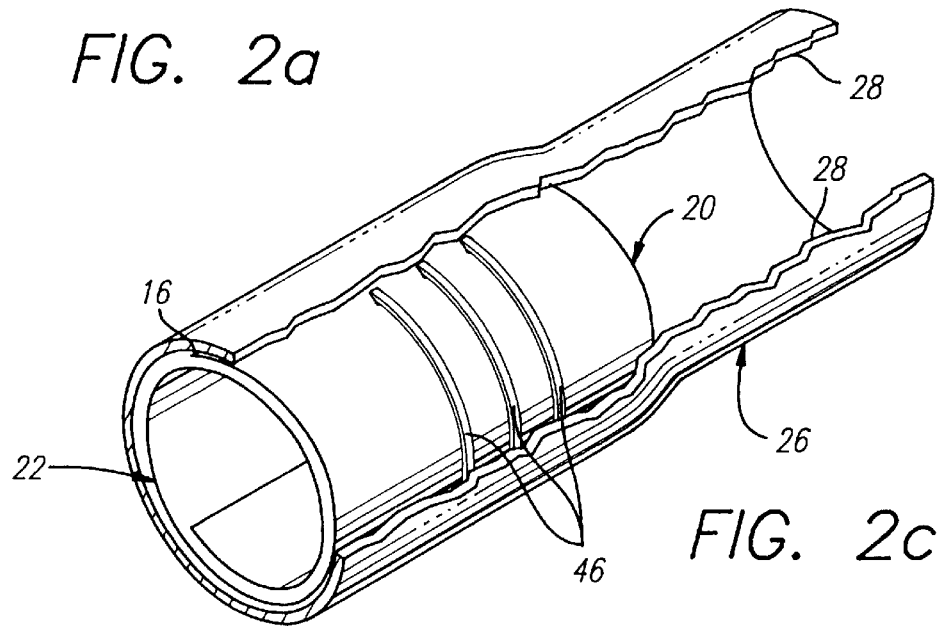

REMOVABLE STENT AND METHOD OF DEPLOYMENT

BACKGROUND OF THE INVENTION

1. Field of the Invention

The present invention generally relates to endoprosthesis devices, generally referred to as stents, adapted to be implanted in a body lumen. More particularly, the present invention relates to an expandable stent that can be deployed in and later removed from a body lumen and to a catheter for implanting and removing the stent from the body lumen.

2. Description of Related Art

Tubular prosthesis, commonly known as stents, have been used to reinforce weakened body lumens such as the urethra, bile ducts, blood vessels, the trachea, coronary arteries, and the esophagus. Stents are generally cylindrically shaped devices that are placed within a weakened or damaged section of body lumen to hold the lumen open.

In one application, stents have been widely used to relieve the acute urinary retention symptomatic of prostate disease. In such applications, a stent is positioned within the urethra to prevent deformation of the urethral wall that might otherwise result from the pressure exerted on the urethra by the hypertrophied prostate gland.

In typical urethral stenting procedures, the stent is transurethrally inserted and positioned within the desired portion of the urethra. In order for a stent to be used most advantageously, it is desirable for the stent to have a delivery diameter that is substantially smaller than the diameter of the body lumen. Upon deployment, the stent should assume a deployed diameter that is essentially equal to the diameter of the body lumen.

The use of stents in the urethra creates special problems. Minerals suspended in the urine can cause encrustation on the stent internal walls that may eventually block the flow of urine through the stent. Epithelialization, where the cells of the urethra grow over the stent, can complicate or even prevent the removal of the stent. Undesirable movement, also known as migration, of the stent from its desired location may prevent the stent from properly supporting the desired portion of the urethra. In some cases, a migrating stent can block or injure the urethra itself. A migrating stent may also cause incontinence, such as when a stent migrates to a position in the urethra between the distal sphincter.

Examples of intraurethral and other intraluminal stents can be found in U.S. Pat. Nos. 4,740,207 (Kreamer); 4,877,030 (Beck et al.); 5,059,211 (Stack et al.); 5,078,726 (Kreamer); 5,192,307 (Wall); 5,306,294 (Winston et al.); 5,354,309 (Schnepp-Pesch et al.); and 5,383,926 (Lock et al.), which are incorporated herein by reference in their entirety. These patents by no means make up the entire body of art relating to stents, and are referred to herein by example only.

Metallic mesh stents, in the form of an expandable mesh tube, have been used to treat urethral strictures as well as for problems in other body lumens. Metallic mesh stents may be self-expanding, depending on the specific design and materials.

During expansion of a metallic mesh stent, the increase in the stent's deployment diameter is accompanied by a substantial decrease in axial length. As the stent diameter expands and contacts the walls of the body lumen, the stent contracts longitudinally. This longitudinal contraction can create undesirable axial stress in the body lumen and makes precise positioning of the stent difficult. An improperly positioned stent can cause various problems, including incontinence and urethral obstruction.

Metallic mesh stents typically endothelialize or incorporate into the urethral wall, thus becoming permanently implanted. The cells of the body lumen wall typically begin to grow into the gaps in the wire-mesh within 1 to 2 weeks. In many cases, the walls of a wire-mesh stent will be entirely enclosed by the wall's cells. In such cases, removal of the stent may be extremely difficult and in some cases impossible without causing substantial trauma to the body lumen.

Another permanently implanted urethral stent is the so-called ASI stent, which comprises a one-piece structure formed of titanium. The ASI stent loosely approximates a wire-mesh stent, but is formed from a single cylindrical sheet instead of numerous wires. Thus, the ASI stent avoids the presence of sharp wire ends. The ASI stent is rigid and must be expanded with a balloon or similar expansion mechanism. Like the wire mesh stents, the urethral epithelium grows through the openings in the ASI stent outer wall, thus permanently implanting the stent into the urethral wall.

Removal of a deployed stent is of particular concern. Such removal may be necessary due to pain, infection, or migration of the stent. Removal may also be necessary where the stent is no longer required, as in the case where the body lumen has fully recovered from the event that initially weakened or constricted the lumen.

Some stents have been designed to allow for later removal. However, such removal is typically allowed only for a brief time immediately following implant of the stent, before the cells of the body lumen begin to encapsulate the stent. Additionally, the removal process is often difficult and hazardous. For example, removing wire mesh stents typically involves grasping the stent with a plier and pulling the stent into a catheter. However, as the stent is drawn into the catheter, the stent typically scrapes against the body lumen, thereby causing trauma to, and possible weakening of, the body lumen.

Devices for deploying and removing stents include various catheters. Typical deployment methods involve slipping the cylindrical stent, in delivery configuration, around the distal end of the deployment catheter. The catheter is then introduced into the body lumen. When the stent is in the proper location for deployment, the stent is deployed so as to expand to contact the walls of the body lumen. In other deployment catheters, a self-expanding stent is held within a sheath on the catheter. With the sheath positioned adjacent to the deployment location, the stent is pushed out of the sheath, whereupon the stent expands to its deployed configuration.

Removal techniques often are complex and cause trauma to the body lumen. Additionally, many removal methods involve destroying the stent during the removal process. Such destruction is not compatible with merely relocating the stent.

Further details of deployment and removal catheters can be found in U.S. Pat. Nos. 4,969,890 (Sugita et al.); 5,089,006 (Stiles); 5,100,429 (Sinofsky et al.); 5,147,385 (Beck et al.); 5,192,297 (Hull); 5,242,451 (Harada et al.); and 5,312,339 (Boussignac et al.), which are incorporated herein in their entirety by reference.

What has been needed and heretofore unavailable is a stent and catheter that allow the stent to be deployed and removed from the body lumen quickly and easily, with minimal trauma to the body lumen. The present invention meets these needs.

SUMMARY OF THE INVENTION

Preliminarily, it should be noted that the terms "distal" and "proximal" are relative terms, with centers of reference that depend on the object involved. Operating tools and devices such as catheters and stents typically are proximally centered on the surgeon. Accordingly, the proximal end of the catheter is the end that is closest to the surgeon, whereas the distal end of the catheter is the end that is inserted into the patient. In contrast, parts of the patient's body, such as the body lumen, reference the patient as the proximal center. Accordingly, the proximal end of the urethra is the end nearest the bladder, i.e., furthest inside the patient, while the distal end is the discharge orifice at the penis.

Additionally, the term "implant" refers to placing a device in the body with the device remaining in the body for at least one day. Similarly, "implantable" is used in this application to describe devices that are left in the body for at least one day.

The present invention is directed toward an improved stent and corresponding deployment and removal catheters. The invention provides a stent for removable deployment in a body lumen. The stent may be deployed intraluminally at a desired position in the body lumen using a deployment catheter, with the deployment catheter preventing the stent from prematurely deploying prior to reaching the proper position in the body lumen. Moreover, the stent can be removed from the body lumen via a removal catheter, with removal occurring several months after initial deployment of the stent. Removal is achieved so as to minimize the risk of causing trauma to the walls of the body lumen.

The stent has a generally cylindrical body or core, sized to be removably implanted in a body lumen. More specifically, the stent is a tubular member with a distal end and a proximal end. The stent is formed from a thin, generally rectangular panel or sheet that has been wound about itself to form a generally cylindrical roll or coil.

The stent has a deployed configuration, which is the configuration the stent holds when it has been implanted in the body lumen. The deployed diameter of the stent is essentially the same as the inside diameter of the body lumen.

The stent in its deployed configuration is generally too large in diameter to be transported to the deployment position without causing severe trauma to the body lumen. Accordingly, in order to reduce the diameter of the stent to allow its delivery to the deployment site, the stent has a delivery configuration that has a significantly smaller diameter than the deployed configuration.

To achieve the delivery diameter, the stent is wound into a tight roll or coil having a diameter that is a fraction of the body lumen diameter or of the stent deployed diameter.

The low profile delivery diameter allows the coiled stent to be intraluminally introduced and positioned at a desired deployment location in the body lumen. Upon deployment, the stent is biased toward its unrolled state, so that it partially unrolls or uncoils, thereby expanding radially outward to achieve its deployed diameter.

The stent is typically formed of a memory-shape alloy such as nickel-titanium (NiTi) that remembers the flat, unrolled configuration. Upon exposure to body heat, the stent biases toward the unrolled configuration, radially expanding until it contacts and exerts outward pressure on the walls of the body lumen and as it assumes its deployed configuration.

The patient's body heat will cause the shape-memory alloy of the stent to quickly transform and expand the stent from its delivery configuration to its deployed configuration. Since the stent when deployed is biased toward its flat configuration, the stent expands radially outward until its presses firmly against the urethra walls. This outward pressure from the stent aids the body's ability to open the urethra and void.

In one embodiment of the invention, the rectangular sheet of the stent is tapered toward the outer side edge. Thus, when the sheet is wound into a cylindrical shape, the tapered edge reduces the resilience of the sheet near the tapered edge, so that the edge is less likely to be levered outward from the main body of the stent.

In an alternate embodiment of the invention, the side edges of the stent are feathered. This feathering helps the edges to more closely coil against the cylindrical body of the stent and more closely approximate a curved surface than would a side edge having a uniform thickness.

The stent may have a filament attached at an inner edge. When the stent is deployed in the body lumen, the filament passes from the stent and along the body lumen. The filament can be used to facilitate subsequent removal of the stent.

The sheet is preferably a continuous panel, without holes or other interruptions in its surface. Thus, the outer surface of the stent is essentially smooth and continuous. This prevents endothelialization, wherein cells of the body lumen might grow into holes that might otherwise be present in the surface of the stent.

In one embodiment of the invention, the stent has a coating that resists encrustation and cell growth. Such a coating may include a biologically neutral metal, such as silver, placed on the stent by ion bombardment. The coating reduces the chance of infection and resists endothelialization.

In an alternative embodiment, the stent has at least one lateral support rib that extends laterally around the wound stent. The support rib strengthens the stent against the constricting forces of the body lumen that might otherwise cause the stent to collapse radially inward. Additionally, the rib increases the outward force against the body lumen wall. Similar strengthening of the stent may also be achieved by increasing the thickness of the central portions of the rectangular sheet that forms the stent.

The stent may be rigid or flexible, depending on the particular application. A flexible stent can flex with the body lumen during physical movements by the patient.

The deployment catheter secures the stent while the stent is positioned within the body lumen. The catheter may include a cooling means, such as a flow of saline solution, for maintaining the stent below body temperature during positioning, thereby preventing premature deployment of the stent. In one embodiment, the deployment catheter includes a locking system for physically preventing the stent from prematurely transforming to its deployed configuration.

The removal catheter allows the stent to be removed with minimal trauma to the body lumen. In one embodiment, the removal catheter has a sheath and a pair of pincer grips. The pincer grips grasp an edge of the implanted stent. By rotating the pinched edge of the stent, the pincer causes the stent to telescopically coil into a smaller diameter so that the stent can be pulled into the sheath. The catheter can then be withdrawn, thereby withdrawing the stent.

In another embodiment, the removal catheter has a cannula in lieu of pincer grips. The stent has a filament attached to it and the cannula is introduced into the body lumen following along the filament. With the sheath and cannula positioned adjacent to the deployed stent, the stent is coiled onto the cannula. By pulling on the filament, the stent is pulled into the sheath.

Both the deployment and removal catheters may be rigid or flexible, depending on the particular application. A flexible catheter may more easily follow turns of the body lumen and reduce trauma to the body lumen walls.

These and other aspects and advantages will become apparent from the following detailed description, and the accompanying drawings, which illustrate by way of example the features of the invention.

BRIEF DESCRIPTION OF THE DRAWINGS

FIG. 1 is a perspective view depicting a stent according to the present invention in its delivery configuration.

FIG. 1a is a perspective view depicting the stent of FIG. 1 in a flat, unrolled configuration.

FIG. 1b is a cross-sectional side view depicting the stent of FIG. 1 in a flat, unrolled configuration.

FIG. 1c is a perspective view depicting the stent of FIG. 1 in its deployed configuration.

FIG. 2 is a perspective view depicting a stent according to another embodiment of the present invention in its delivery configuration.

FIG. 2a is a perspective view depicting the stent of FIG. 2 in a flat, unrolled configuration.

FIG. 2b is a cross-sectional side view depicting the stent of FIG. 2 in a flat, unrolled configuration.

FIG. 2c is a perspective view depicting the stent of FIG. 2 in its deployed configuration.

DETAILED DESCRIPTION OF THE PREFERRED EMBODIMENTS

Figure 3:
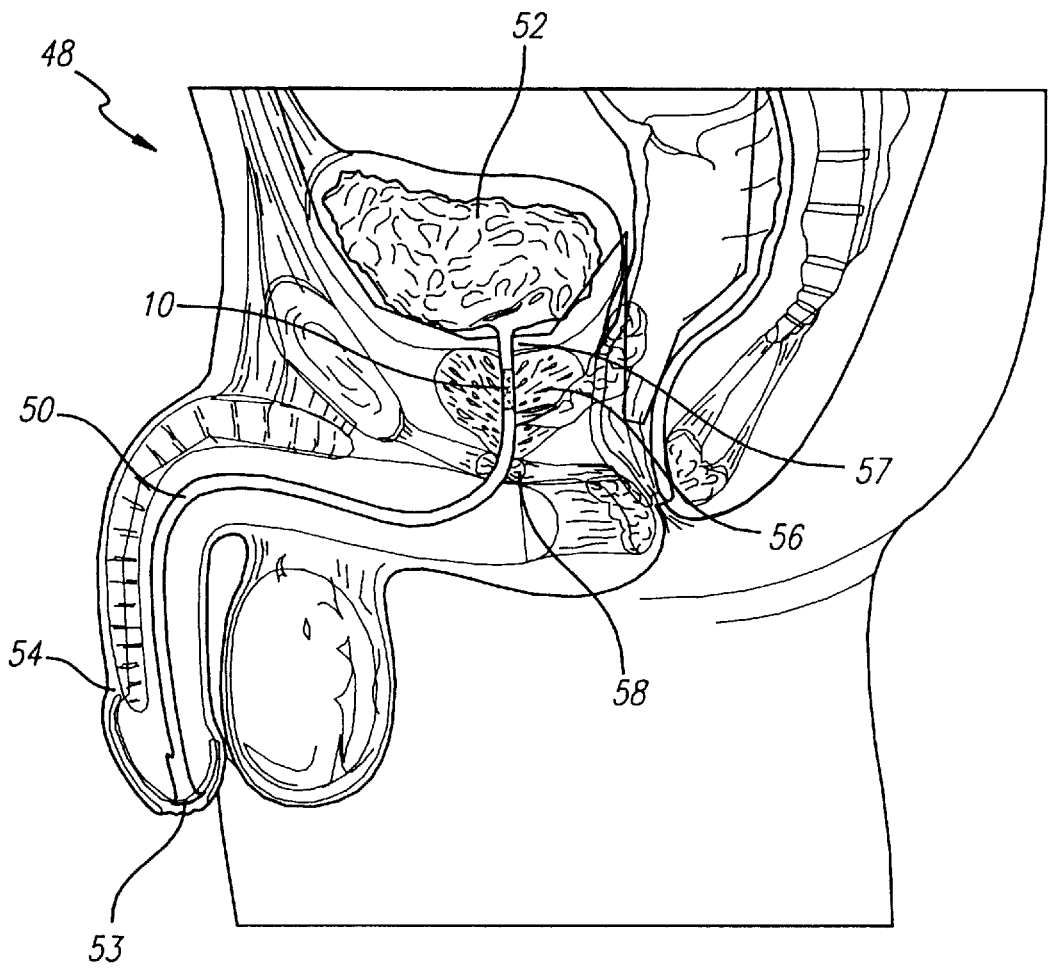
FIG. 3 is a cross-sectional side view of a patient showing a stent deployed in the patient's urethra.

The present invention is depicted in FIGS. 1–9 for use in various body lumens, including use in reinforcing the urethra against pressure caused by a hypertrophic prostate gland. However, the present invention is not limited to urethras, but can be used in other body lumens as well.

Referring to FIG. 1, in one preferred embodiment the stent 10 is formed from a generally rectangular sheet 12 having end edges 14 and side edges 16, 18. The sheet 12 has been wound upon itself in a counterclockwise winding direction, with the outer side edge 16 passing over the inner side edge 18, to form a generally cylindrically-shaped stent 10 having a distal end 20 and a proximal end 22.

FIG. 1 shows the stent 10 in its delivery configuration. In the delivery configuration, it is desirable for the stent 10 to be sufficiently small so as to, when secured to a catheter or other deployment device, easily pass within the body lumen 26 without unnecessarily engaging the body lumen walls 28.

In the present invention, the sheet 12 has been wound tightly so as to create a stent 10 with a delivery diameter 24 substantially smaller than the diameter 30 of the body lumen 26. In the embodiment shown, the delivery diameter 24 is on the order of 3 millimeter (0.1101") or less.

FIGS. 1a and 1b show the rectangular sheet in a flat, unrolled configuration. To achieve a small delivery diameter, the thickness 31 of the rectangular sheet 12 is on the order of 0.002 inch. In the embodiment shown, the outer side edge 16 of the stent 10 is tapered. A non-tapered side edge can create an additional disruption on the otherwise cylindrical outer surface of the stent 10. In contrast, the tapered outer side edge 16 allows the stent 10 to more closely approximate a curved or cylindrical outer surface. To further reduce the risk of trauma to the body lumen 26, the corners 29 of the stent 10 may be rounded.

The sheet 12 is preferably sufficiently thin, and formed of appropriate material, to allow the stent 10, when implanted in a living body, to flex in response to muscle flexing, sphincter flexing, and high liquid flow rates.

The stent 10 of FIG. 1 may include a filament 32, with said filament being secured to the stent at a hole 34 or similar attachment point on the stent 10. The filament 32 may comprises a non-absorbable nylon suture. In the embodiment shown, the hole 34 is located near the intersection of the outer side edge 16 and the stent proximal end 22. As will be discussed in greater detail below with respect to FIG. 8, the filament 32 is helpful in removing the stent 10 from the body lumen 26.

The stent 10 of the present invention preferably is made of a shape-memory alloy, such as nickel-titanium shape-memory alloy, which has a martinsitic metallurgical state and an austenitic metallurgical state, and a transition temperature therebetween. Shape-memory alloys are known in the art and are discussed in Shape-Memory Alloys, Scientific American, Volume 281, pages 74–82 (November 1979), incorporated herein by reference.

Shape-memory alloys undergo transition between an austenitic state and a martinsitic state at certain temperatures. When deformed while in the martinsitic state they will retain this deformation as long as they are retained in this state. However, when heated to the transition temperature, they transform to their austenitic state whereupon they will revert to their original configuration. The transition temperature depends on the nature of the alloy and the condition of the material. Nickel-titanium-based alloys (NiTi), wherein the transition temperature is slightly lower than the body temperature, are preferred for the present invention. It is desirable to have the transition temperature set at just below the body temperature to insure rapid transition from the martinsitic state to the austenitic state when the stent 10 is implanted in a body lumen.

As described with respect to FIG. 1, the stent 10 is in a martinsitic metallurgical state, and is wound tightly into its delivery configuration. The stent 10 will retain its delivery configuration as long as the temperature to which it is exposed remains somewhat below body temperature (approximately 98 degrees F.). When exposed to body temperature, the stent 10 will be biased toward its flat, unrolled configuration and will rapidly transform to its deployed configuration shown in FIG. 1c.

FIG. 1c shows the stent 10 of FIG. 1 axially expanded to its deployed configuration. In this embodiment, the deployed stent 10 has a deployed diameter 36 essentially equal to the diameter 30 of the body lumen 26. The stent 10 when deployed is biased toward its flat, unrolled configuration. Accordingly, the outer surface 38 of the stent 10 firmly engages against the walls 28 of the body lumen 26.

The tapered outer side edge 16 allows the outer surface 38 of the stent 10 to more closely approximate a cylinder. Tapering also prevents the outer side edge 16 from levering itself away from the main body of the stent 10. A thicker side edge may be biased outwardly with greater force due to the increased strength of the thicker material, which might cause the outer side edge 16 to force itself slightly outward from the main body of the stent 10. The thinner material of a tapered edge has less outward bias, and thus the pressure from the walls 28 of the body lumen 26 can more easily force the outer side edge 16 inward against the main body of the stent 10.

The inner side edge 18 may also be tapered, with the primary motivation for such tapering being to allow the inner surface 40 of the stent to form an axial passage 42 that more closely approximates a cylindrical passage, without unnecessary disruptions in the inner surface 40. Reducing disruptions on the inner surface 40 can help to reduce turbulence in the liquid flow through the axial passage 42, as well as prevent particles from adhering to the inner surface 40.

The outer surface 38 of the stent 10 in the deployed configuration is interruptions, and with minimal interruptions, and having no holes therethrough. This prevents endothelialization, whereby tissue from the body lumen walls might otherwise grow into holes in the outer surface 38. Such endothelialization complicates, and sometimes renders unfeasible, subsequent removal of the stent 10 from the body lumen 26.

Due to the wound construction of the stent, the length 44 of the stent does not vary between delivery and deployment. The delivery length and the deployed length are essentially identical. The length of any one stent depends on the particular application. For example, a stent for use in a urethra would generally have a length on the order of 1 to 6 cm.

The deployed stent 10 may be curved or tapered, as opposed to a perfect cylinder, to conform to the prostatic urethral cavity, which is often curved.

In transforming from the delivery to the deployed configuration, the stent "unwinds" in a clockwise direction, i.e., in a direction opposite to its direction of winding. For purposes of this specification, the winding direction of the stent is defined as the direction in which the outer side edge 16 passes, with respect to the axial center of the stent 10, when the sheet 12 of the stent 10 is wound into its generally cylindrical shape.

The stent may additionally include a coating to reduce encrustation and endothelialization. One embodiment involves coating the stent 10 with a material known as SPI-ARGENT™. SPI-ARGENT™ is produced by the Spire Corporation, 1 Patriot Park, Bedford, Mass. In one embodiment of the invention, SPI-ARGENT™ is applied to the stent through an ion bombardment process. Ion bombardment allows the coating to penetrate the stent surface for better adherence. The coating so described reduces the possibility of infection while resisting encrustation and endothelialization. The coating typically constitutes a thickness of 3000 angstroms.

In an alternate form of the invention, as depicted in FIGS. 2, 2a, 2b, and 2c, the stent 10 is formed having an outer side edge 16 that is feathered. FIG. 2 shows the stent in its delivery configuration, FIGS. 2a and 2b show the unrolled configuration, and FIG. 2d shows the deployed configuration.

FIGS. 2a and 2b show the rectangular sheet 12 in a flat, unrolled configuration. The thickness 31 of the sheet 12 is small to allow for a small delivery diameter when the sheet 12 is formed into a roll.

The feathering of the outer side edge 16 allows the stent 10, when in rolled configuration, to more closely approximate a cylindrical surface. The feathering also weakens the resilience of the sheet 12 adjacent to the outer side edge 16, thereby reducing the tendency of the outer side edge 16 to cantilever outwardly from the main body of the stent 10.

The embodiment of FIG. 2 additionally has a series of support ribs 46 spanning a portion of the sheet 12. These ribs 46 strengthen the stent against radial pressures from the body lumen walls 28 that might otherwise cause the stent 10 to collapse inwardly. A similar strengthening may be achieved by making the central portions of the sheet 12 of increased thickness.

An example of how a stent 10 is deployed in a body lumen is depicted in FIGS. 3, 4, 5, and 6. FIG. 3 depicts the stent 10 deployed in a patient 48, and specifically in the urethra 50 of the patient 48. The urethra 50 passes from the bladder 52 to the distal urethral orifice 53 at the penis 54. Just below, or distally of, the bladder 52, the urethra 48 passes through the prostrate 56. The flow of urine is controlled by the proximal sphincter 57 and the distal sphincter 58.

Where the prostrate 56 is enlarged, as may occur in various circumstances, the prostrate 56 presses against the urethra 50, which can cause partial or even total blockage of the urethra 50. The stent 10 can be positioned within the urethra 50 where it passes through the prostate 56 to hold the urethra 50 open.

In FIG. 3, the stent 10 is depicted positioned in the urethra 50 between the distal sphincter 58 and the proximal sphincter 57. However, the positioning of the stent 10 depends on various factors, including the body lumen involved and the particular condition being treated. Even where a particular condition is being treated, such as a hypertrophied prostate gland, the precise positioning of the stent 10 can vary depending on the individual patient as well as the particular surgeon.

Figure 4:
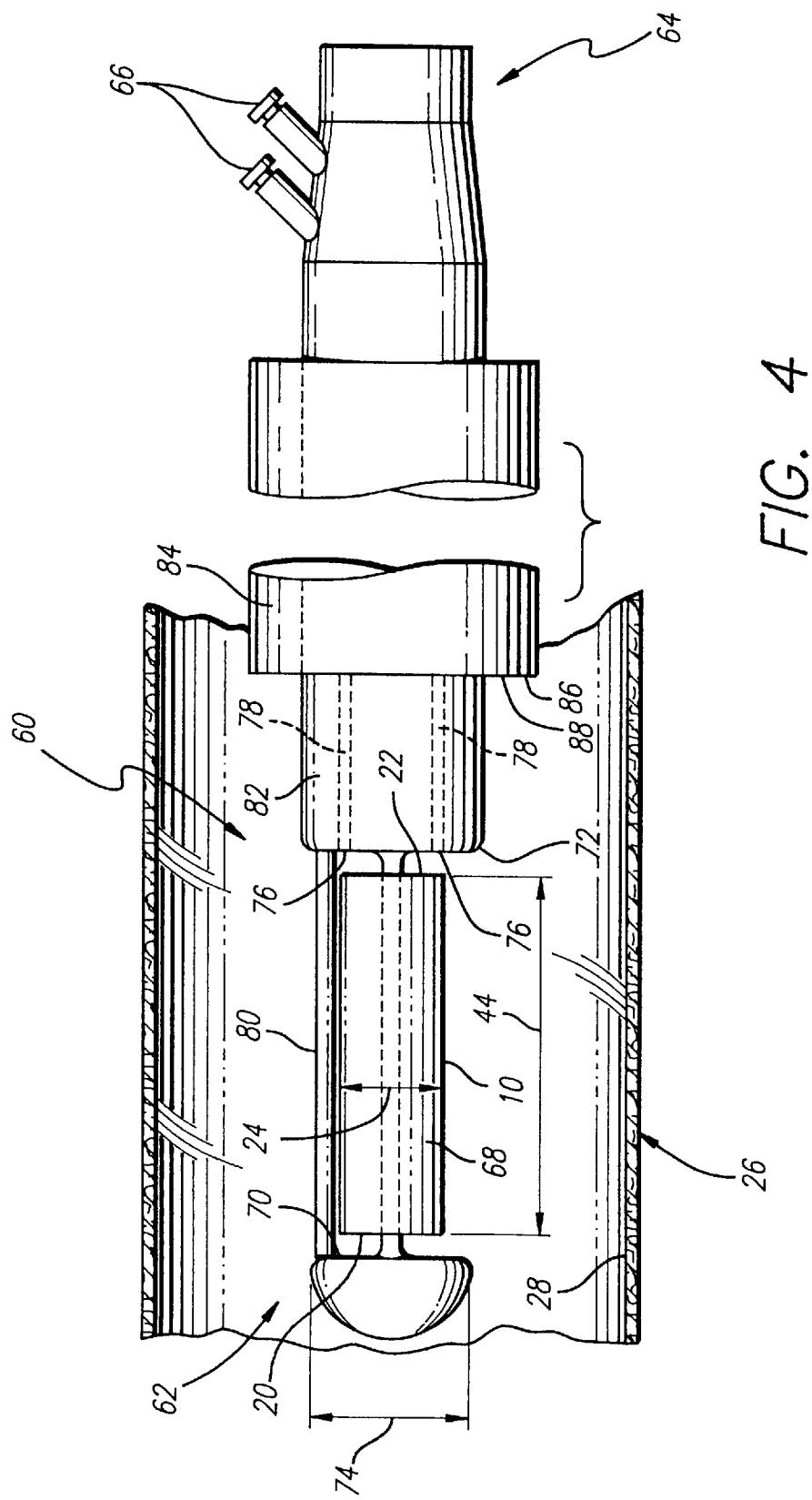
FIG. 4 is a side view of a stent deployment catheter according to the present invention.
Figure 5:
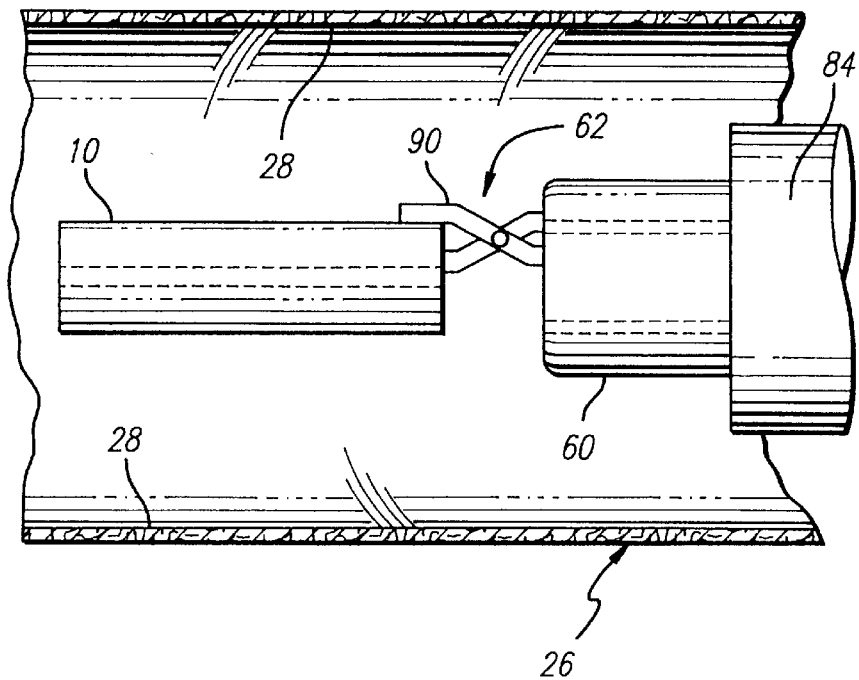
FIG. 5 is a side view of a stent deployment catheter according to another embodiment of the present invention.
Figure 6:
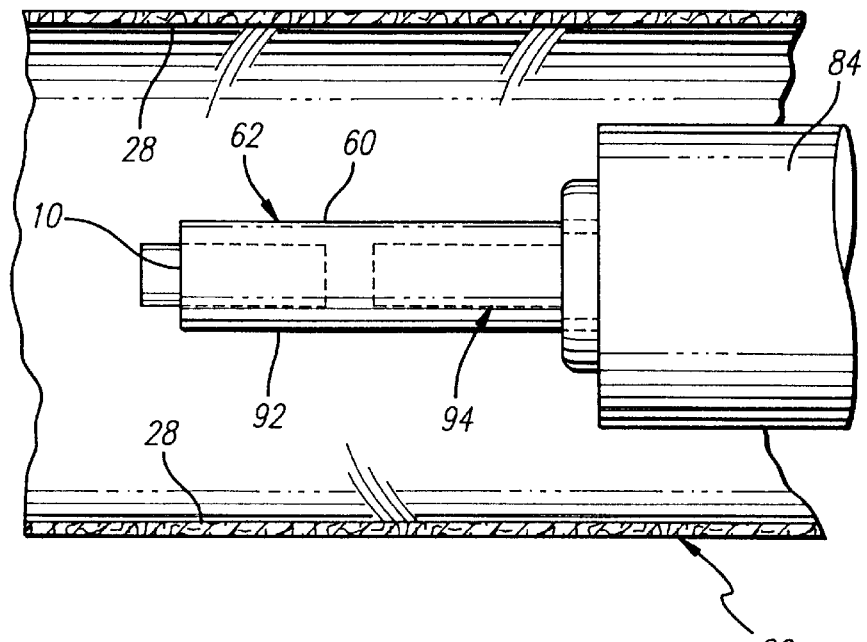
FIG. 6 is a side view of a stent removal catheter according to the present invention.

FIGS. 4, 5, and 6 depict the stent deployed in a body lumen. Referring to FIG. 4, the stent 10 is secured to a deployment catheter 60. The deployment catheter 60 has a distal end 62 and a proximal end 64, with the catheter controls 66 located at the proximal end 64 for access by an operating surgeon. The catheter 60 may be rigid or flexible.

The stent 10 is shown secured to the distal end 62 of the deployment catheter 60. The stent 10 is wound onto the deployment catheter 60 about an annular depression 68 generally sized to accommodate the length 44 and delivery diameter 24 of the stent 10. The annular depression is generally defined by a distal annular shoulder 70 and a proximal annular shoulder 72.

The distal end 62 of the deployment catheter 60 is generally smooth and rounded to reduce the risk of damaging the body lumen. The distal end 62 has a diameter 74 greater than the delivery diameter 24 of the stent 10. Accordingly, the stent 10 does not extend radially outward from the deployment catheter 60. Otherwise, the distal end 20 of the stent 10 might rub against and damage the body lumen walls 28 during delivery.

The deployment catheter 60 preferably includes means for supplying coolant to the stent during the delivery process. The delivery of the coolant prevents the stent 10 from warming to body temperature during the delivery process, which might otherwise cause premature deployment of the stent 10. In the embodiment of FIG. 4, the deployment catheter 60 has small outlet holes 76 through which a coolant, such as a saline solution, is discharged. The saline solution passes through the deployment catheter 60 through a series of fluid passageways 78 that lead to the outlet holes 76. The outlet holes 76 are located so that the coolant is discharged so as to flow onto the stent 10. When the coolant flow is halted, the stent 10 warms to body temperature and becomes biased towards the unrolled configuration. Accordingly, the stent 10 will unroll into its deployed configuration.

In FIG. 4, the deployment catheter 60 supplies the flow of coolant. However, the coolant may alternately be provided by another source, such as another catheter positioned in the body lumen 26.

In the embodiment of FIG. 4, the stent 10 is physically secured onto the deployment catheter 60 by a locking pin 80. The locking pin 80 shown extends from the proximal annular shoulder 72 to the distal annular shoulder 70, passing axially outward from the stent 10 in delivery configuration. If the stent 10 begins to deploy prematurely, as may occur if the stent 10 is exposed to body temperature prior to being in proper position within the body lumen 26, the locking pin 80 acts as a physical barrier to prevent axial expansion of the stent 10.

To unlock the stent 10 from the deployment catheter 60, the locking pin 80 slides away from the distal annular shoulder 70 and into a retracting slot 82 in the proximal shoulder 72. Once the locking pin 80 has slid back clear of the proximal end 22 of the stent 10, the stent 10 is no longer physically constrained in its delivery configuration. Accordingly, the stent 10 can then expand radially to assume its deployed configuration.

To further reduce trauma to the body lumen 26, the deployment catheter 60 is typically introduced into the body lumen 26 through a guide catheter 84. The guide catheter 84 protects the body lumen 26 from unnecessary trauma that might be caused by repeated insertion, removal, and other movement of the deployment catheter 60 as well as other catheters that may be necessary during a particular surgical procedure. The distal end 86 of the guide catheter 84 is typically positioned just before the site in the body lumen 26 where the stent 10 is to be deployed, so to protect distal regions of the body lumen 26 while still allowing access to the deployment site. To access the deployment site, the deployment catheter 60 passes through an axial passage or lumen 88 in the guide catheter 84.

In another preferred embodiment, as shown in FIG. 5, the distal end 62 of the deployment catheter 60 has a pincer grip 90 (commonly referred to as a grasper) for holding the stent 10 in its delivery configuration. Prior to insertion of the catheter into the body lumen 26, the stent 10 is secured, in its delivery configuration, in the grasp of the pincer grip 90. The distal end 62 of the deployment catheter 60 is then inserted into the body lumen, typically through a guide catheter 84, until the stent 10 is at the deployment position.

With the stent 10 in the deployment position, the pincer grip 90 is opened to release the stent 10. If the deployment process involves cooling the stent 10 during the delivery process, the flow of coolant is typically stopped at about the same time as the pincer grip 90 is opened. When the stent 10 is warmed to body temperature and free of the pincer grip 90, the stent 10 becomes biased toward the unrolled configuration and, accordingly, will expand to its deployed configuration. Depending on the particular shape-memory metal involved, the stent 10 may expand very rapidly, i.e., within 1 or 2 seconds, to its deployed configuration once exposed to body temperature.

FIG. 6 shows another preferred embodiment of a deployment catheter 60. The deployment catheter 60 has a sheath 92 which is sized to receive the stent 10 in its delivery configuration. The stent 10 is slid into the sheath 92 and introduced into the body lumen 26. The deployment catheter 60 is positioned such that the sheath 92 is just below the deployment position of the stent 10. The catheter 60 may be rigid, or it may be flexible to allow it to more easily pass through a curved body lumen.

With the deployment catheter 60 properly positioned, the stent 10 is pushed out of the sheath 92 by a push rod 94 or other device. Once free of the constraints of the sheath 92, the stent 10 rapidly expands to its deployed configuration.

Figure 7:
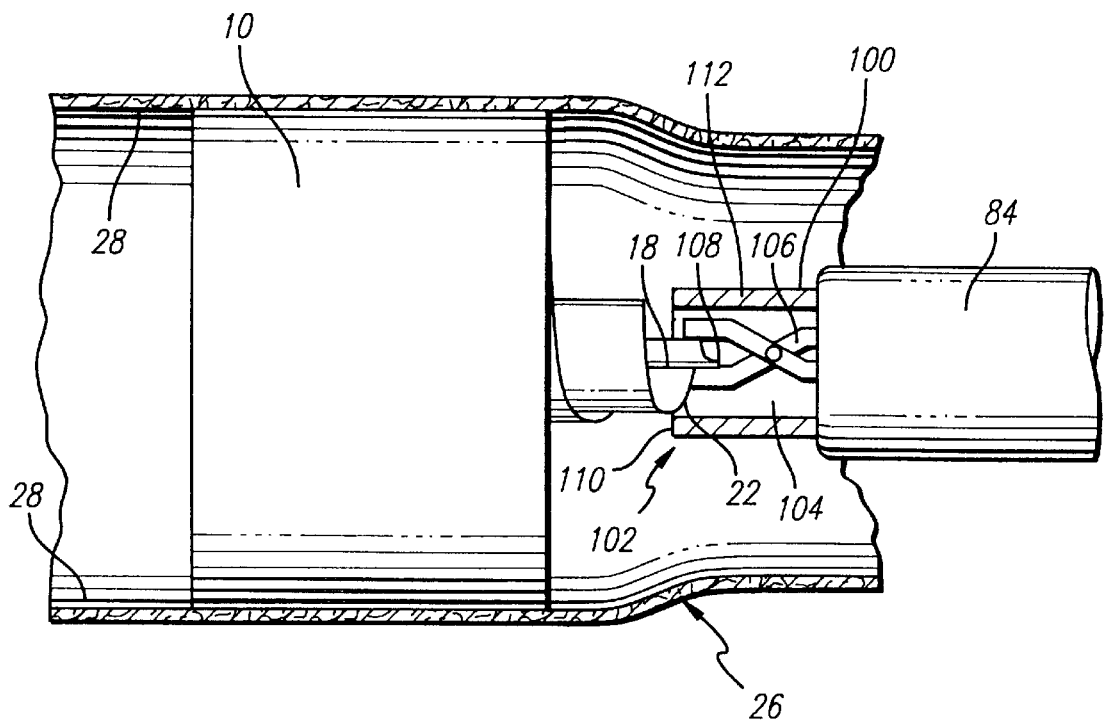
FIG. 7 is a side view of a stent removal catheter according to another embodiment of the present invention.
Figure 8:
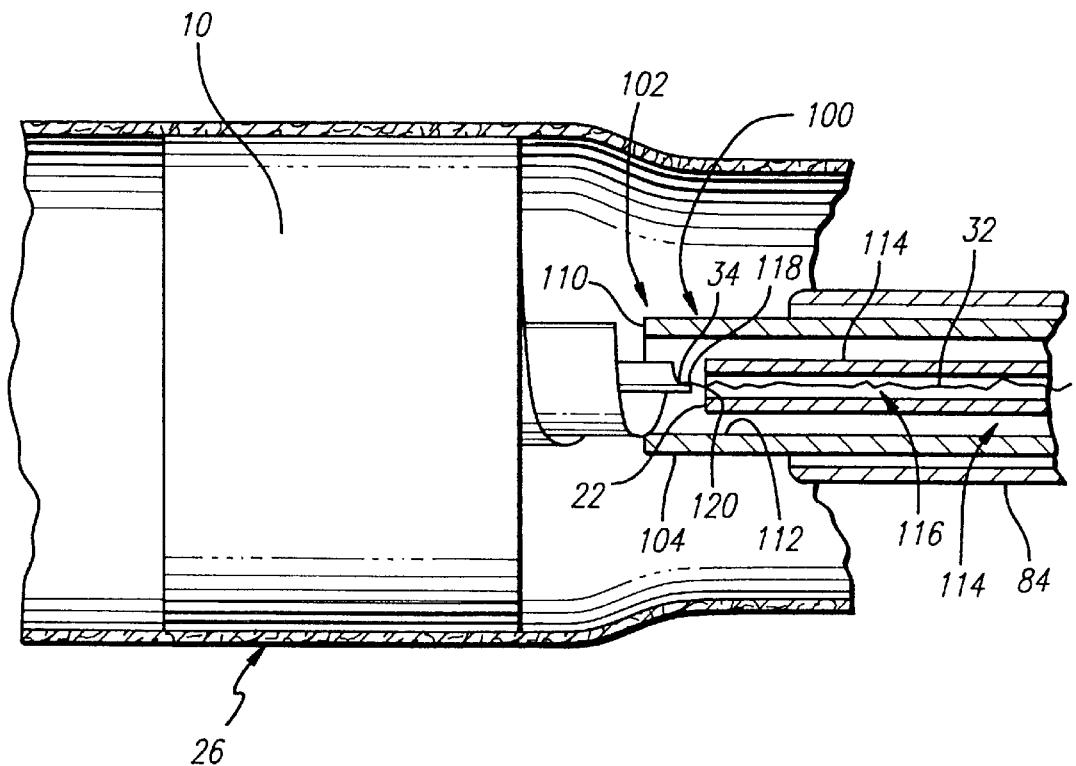
FIG. 8 is a side view of a stent removal catheter according to another embodiment of the present invention.

FIGS. 7 and 8 depict preferred embodiments of a catheter 100 for removing the deployed stent 10 from the body lumen 26. Referring to FIG. 7, a removal catheter 100 has a distal end 102 with a sheath 104 at the distal end. The catheter 100 may be rigid or flexible.

A pincer grip 106 slidingly extends from the sheath 104 and seizes the stent 10 at a point 108 near the inner side edge 18 and proximal end 22 of the stent. Once the stent 10 is secure in the grasp of the pincer grip 106, the pincer grip 106 slidingly withdraws back into the sheath 104. As the pincer grip 106 is withdrawn, it pulls the stent 10 back into the sheath 104. The proximal edge 22 of the stent 10 contacts the distal end 110 and interior walls 112 of the sheath 104, forcing the stent 10 to wind telescopically upon itself to fit within the sheath 104.

As the pincer grip 106 is withdrawn into the sheath 104, the pincer grip 106 may rotate in a direction counter to the winding direction of the stent 10. This rotation facilitates the axial winding of the stent 10, thus hastening the retraction of the stent 10 into the sheath 104.

Similarly, the sheath 104 itself may be rotated as the stent 10 is withdrawn. However, the sheath 104 should be rotated in a direction opposite to the rotation of the pincer grip 106.

If both the sheath 104 and pincer grip 106 are rotated at the same time, the counterrotation causes the stent 10 to withdraw into the sheath 104 quickly and with minimal trauma to the body lumen 26.

Using the removal catheter 100 in the embodiment of FIG. 7, removal of the stent 10 is preferably performed with the assistance of a cystoscope having optics allowing the surgeon to properly view the stent 10 and pincer grip 106 in order to guide the process of seizing the stent 10.

Controls for the removal catheter are preferably located at the proximal end (not shown) of the removal catheter to allow the surgeon to conveniently manipulate the controls.

FIG. 8 depicts another preferred embodiment of a removal catheter 100. The removal catheter 100 is designed for use with a stent 10 having a filament 32 attached thereto. The filament 32 extends along the body lumen, preferably distally from the stent 10. For example, in urethral applications, the filament 32 extends from the stent 10 in a direction away from the bladder, i.e., toward the urethral discharge outlet at the penis. In such an application, the filament 32 may even extend out of the penis, allowing the operating surgeon easier access to the filament 32.

The filament 32 is secured to the stent 10 at a hole 34 situated near the inner side edge 18 and the proximal end 22. Thus, the filament 32 is secured to the stent 10 at or very near the seizure point 108 described with respect to FIG. 7 where the pincer grip 106 seized the stent 10 where the filament 32 was not present.

A sheath 104 is positioned at the distal end 102 of the removal catheter 100. The removal catheter 100 has a cannula 114 passing axially therethrough, with the cannula 114 having an axial passageway 116 through its length. The cannula 114 is preferably capable of being axially rotated as well as longitudinally slid within the removal catheter 100 and through the sheath 104. The cannula 114 may be rigid or flexible.

As the cannula 114 is introduced into the body lumen 26, which may be performed concurrently with the introduction of the removal catheter 100, the cannula 114 passes around the filament 32, such that the filament 32 is drawn into the cannula 114. During this process, care should be taken not to exert substantial tension on the filament 32, as such tension might cause sufficient pulling force on the stent 10 to cause the stent 10 to prematurely move from its deployed position. Such movement could damage the body lumen 26 and complicate removal of the stent 10.

The removal catheter 100 is positioned such that the distal edge 110 of the sheath 104 is adjacent to the proximal end 22 of the stent 10. The distal edge 118 of the cannula 114 is carefully placed near the filament attachment hole 34 on the stent 10. Sufficient tension is placed on the filament 32 to firmly engage the proximal end 22 of the stent 10 against the cannula 114.

While maintaining sufficient tension on the filament 32 to keep the stent 10 engaged against the cannula 114, the cannula 114 is slid back into the sheath 104, thereby pulling the stent into the sheath. As the cannula 114 is withdrawn, a portion of the proximal end 22 of the stent 10 is pulled against the distal edge 110 of the sheath 104. This contact causes the stent 10 to wind telescopically upon itself, thus facilitating the passage of the stent 10 into the sheath 104.

Concurrently with the withdrawal of the cannula 114 into the sheath 104, the cannula 114 may be axially rotated in a direction opposite to the winding direction of the stent 10. This rotation further facilitates the winding of the stent 10, thereby facilitating the withdrawal of the stent 10 into the sheath 104.

The sheath 104 itself may also be rotated, but in direction opposite to the rotation of the cannula 114. The counterrotation causes the stent 10 to withdraw into the sheath 104 quickly and with minimal trauma to the body lumen 26.

The cannula 114 may be equipped with a slot 120 or other aperture at its distal edge 118, with said slot 120 sized to receive an edge of the stent 10. Thus, when the stent 10 is drawn against the cannula 114, an edge of the stent 10 slides into the slot 120, thus providing a physical connection whereby axial rotation of the cannula 114 directly imparts axial rotation to the edge of the stent 10.

The removal catheter 100 may further include a coordinating means, such as a system of gears, for rendering rotation of the sheath 104 dependent on the rotation of the cannula 114. For example, the sheath 104 and cannula 114 rotation may be coordinated such that a 360 degree counterclockwise rotation of the cannula 114 induces a 180 degree clockwise rotation of the sheath 104. Such coordinating means would allow the surgeon to more easily effect simultaneous rotation of the cannula 114 and sheath 104.

Using the removal catheter 100 in the embodiment of FIG. 8, removal of the stent 10 may be performed with the assistance of a cystoscope having optics allowing the surgeon to view the stent 10 and catheter 100. However, due to the self-guiding nature of the filament 32 in positioning the stent 10 against the cannula 114, the catheter 100 and its method of use allow for the stent 10 to be removed without the use of a cystoscope.

The method of using the removal catheter 100, in both the embodiments of FIG. 7 and 8, may further include flushing the deployed stent 10 with coolant just prior to removal of the stent 10. This can help to weaken the stent 10, and particularly to reduce the stent's bias toward the unrolled configuration, hence facilitating the coiling action as the stent 10 winds into the sheath 104.

Figure 9:
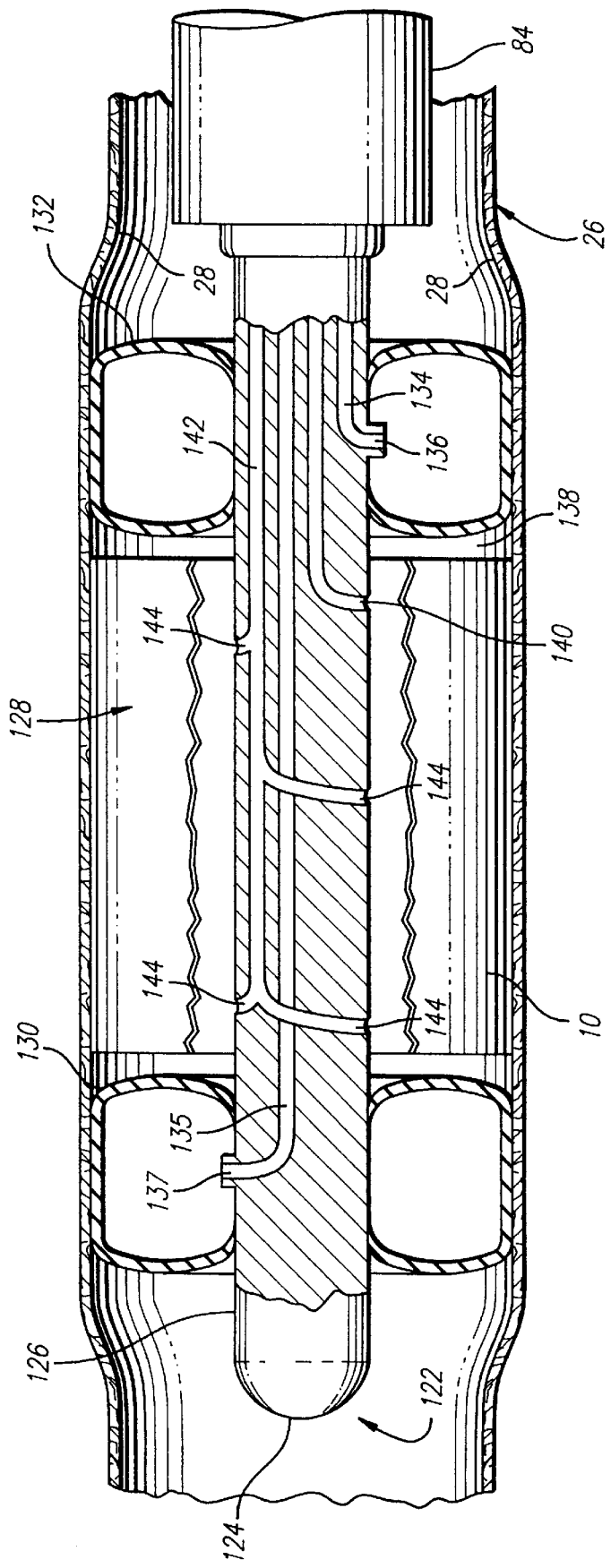
FIG. 9 is a cross-sectional side view of a stent removal catheter according to another embodiment of the invention.

FIG. 9 shows another embodiment of a removal catheter 122. The embodiment of FIG. 9 allows the removal catheter 122 to block the flow of body fluids through the body lumen 26 during removal of the stent 10. With the flow of body fluids blocked, cooling fluid may be more efficiently used to cool the stent 10 below body temperature. Such cooling is useful where a stent 10 is formed from material, such as a shape-memory metal, that biases the stent 10 toward a tightly coiled configuration when the stent 10 is cooled to a temperature below body temperature.

The removal catheter 122 comprises a central shaft portion 126 terminating in a distal end 124. A stent-receiving portion 128 is sized to receive the stent 10 in a removal configuration.

The removal catheter 122 is introduced into the body lumen 26 and positioned such that the stent-receiving portion 128 lies within the implanted stent 10.

On either side of the stent-receiving portion 128 are a distal balloon and a proximal balloon 132. The balloons 130, 132 can be inflated via air or another inflating gas or liquid introduced through ducts 134, 135 that lead to outlets 136, 137 in each balloon 130, 132. The balloons 130, 132 can be individually and separately inflated and deflated.

FIG. 9 depicts the balloons 130, 132 in their inflated state. In their deflated or non-deployed state, the balloons 130, 132 have a diameter approximately the same as the diameter of the removal catheter 122, thus allowing the removal catheter 122 and deflated balloons 130, 132 to easily pass through the body lumen during introduction and removal of the removal catheter 122.

When inflated, the balloons 130, 132 expand radially so that they press against the walls 28 of the body lumen 26, thereby blocking the flow of fluid through the body lumen 26. Each balloon 130, 132 serves as a seal to prevent the flow of fluids into or out of the isolated portion 138 of the body lumen 26 between the balloons 130, 132.

With the balloons inflated, as shown in FIG. 9, the isolated portion 138 of the body lumen 26 can be cleared of residual body fluid via a drain line 140.

The stent 10 in such an embodiment becomes biased toward a tightly coiled configuration upon being cooled to a temperature below the body temperature. To cool the stent 10, cooling fluid is introduced into the isolated portion 138 of the body lumen 26 via coolant ducts 142 and outlets 144. As the cooling fluid enters the isolated portion 138 of the body lumen 26, the stent 10 cools to a temperature where it is biased toward a tightly-coiled state. Accordingly, the stent 10 coils about the stent-receiving portion 128 of the removal catheter 122.

With the stent 10 coiled onto the removal catheter 122, the balloons 130, 132 are deflated and the catheter 122 is withdrawn, thereby removing the stent 10 from the body lumen 26.

While a particular form of the invention has been illustrated and described, it will also be apparent to those skilled in the art that various modifications can be made without departing from the spirit and scope of the invention. For example, a wide variety of materials and dimensions will be adaptable for use in devices according to the present invention. It is not intended that the present invention be limited except by the appended claims.

What is claimed is:

1. A removable intraluminal stent for implantation within a body lumen, the stent having a delivery configuration and a deployed configuration, comprising:

a generally rectangular sheet, said sheet having end edges and side edges, said sheet being wound into a generally cylindrical shape having a distal end and a proximal end, with the side edges overlapping each other in the delivery configuration, said sheet being continuous and endothelialization-resistant wherein at least one of said side edges of said sheet is tapered.

2. The stent of claim 1, wherein at least one of said side edges of said sheet is tapered.

3. The stent of claim 2, wherein said sheet has a uniform thickness of approximately 0.002 inches or less.

4. The stent of claim 1, wherein at least one of said side edges is feathered.

5. The stent of claim 1, wherein said sheet further comprises one or more support ribs.

6. The stent of claim 1, wherein said sheet has an endothelialization-resistant coating on at least a portion of said sheet.

7. The stent of claim 1, wherein the stent is formed from a shape-memory alloy.

8. The stent of claim 7, wherein said shape-memory alloy includes NiTi.

9. A removable intraluminal stent for implantation within a body lumen, the stent having a deployed configuration and a removal configuration, comprising;

a generally cylindrical core, said core comprising a generally rectangular sheet, said sheet having end edges and side edges, said sheet being wound into a generally cylindrical shape having a distal end and a proximal end, with the side edges overlapping each other in the delivery configuration; and wherein said core has an attachment point at which an application of force will bias the stent toward its removal configuration; and a filament secured to the stent at said attachment point whereby pulling on said filament applies force to said attachment point, thereby biasing the stent toward its removal configuration.

10. The removable intraluminal stent of claim 9, wherein said sheet has an unrolled configuration and said sheet is formed from a shape-memory alloy that remembers the unrolled configuration.

11. The removable intraluminal stent of claim 10, wherein said shape-memory alloy includes NiTi.

12. The removable intraluminal stent of claim 9, wherein in the removal configuration said core has a generally telescoping cylindrical shape.

* * * * *

UNITED STATES PATENT AND TRADEMARK OFFICE
CERTIFICATE OF CORRECTION

PATENT NO. : 5,833,707
DATED : Nov. 10, 1998
INVENTOR(S) : John McIntyre, Geoffrey A. Orth, Peter S. Brown It is certified that error appears in the above-identified patent and that said Letters Patent is hereby corrected as shown below:

Column 13, claim 1, starting at line 13, delete "wherein at least one of said edges of said sheet is tapered", replace with --wherein said delivery configuration of said stent has a diameter of less than 0.110 inches--.

Signed and Sealed this

Sixteenth Day of March, 1999

Attest:

Attesting Officer

Q. TODD DICKINSON

Acting Commissioner of Patents and Trademarks